United States Patent [19]
Pahlck et al.

[11] Patent Number: 5,935,557
[45] Date of Patent: Aug. 10, 1999

[54] NAIL BLEACH

[75] Inventors: Harold E. Pahlck, Waldwick; Leona Giat Fleissman, Ridgewood, both of N.J.; Annamaria Vakirtzis, New Windsor, N.Y.

[73] Assignee: Avon Products, Inc., New York, N.Y.

[21] Appl. No.: 08/797,992

[22] Filed: Feb. 12, 1997

[51] Int. Cl.$^6$ .............. A61K 6/00; A61K 7/00; A61K 7/04

[52] U.S. Cl. .............. 424/61; 424/401

[58] Field of Search .............. 424/61, 401, 53, 424/616, 49, 62; 8/115.68; 426/72

[56] References Cited

U.S. PATENT DOCUMENTS

| | | | |
|---|---|---|---|
| 2,197,630 | 4/1940 | Carter | 87/5 |
| 3,257,280 | 6/1966 | Richter | 167/85 |
| 3,510,554 | 5/1970 | Balsiger | 424/61 |
| 3,639,574 | 2/1972 | Schmolka | 424/78 |
| 3,887,702 | 6/1975 | Baldwin | 424/61 |
| 3,954,974 | 5/1976 | Herzog et al. | 424/130 |
| 4,104,333 | 8/1978 | Lee, Jr. et al. | 260/885 |
| 4,260,701 | 4/1981 | Lee, Jr. | 525/303 |
| 4,344,932 | 8/1982 | Gordon | 424/61 |
| 4,626,428 | 12/1986 | Weisberg et al. | 424/61 |
| 4,631,186 | 12/1986 | Brown | 424/61 |
| 4,696,757 | 9/1987 | Blank et al. | 252/186.29 |
| 4,820,509 | 4/1989 | Yamazaki et al. | 424/61 |
| 4,897,261 | 1/1990 | Yamazaki et al. | 424/61 |
| 5,004,599 | 4/1991 | Scher | 424/61 |
| 5,047,249 | 9/1991 | Rothman et al. | 424/543 |
| 5,059,417 | 10/1991 | Williams et al. | 424/53 |
| 5,066,484 | 11/1991 | Castrogiovanni et al. | 424/61 |
| 5,139,570 | 8/1992 | Castrogiovanni et al. | 106/3 |
| 5,217,710 | 6/1993 | Williams et al. | 424/52 |
| 5,254,161 | 10/1993 | DeVido et al. | 106/170 |
| 5,362,488 | 11/1994 | Sibley et al. | 424/78.05 |
| 5,372,802 | 12/1994 | Barrows et al. | 424/52 |
| 5,372,803 | 12/1994 | Williams et al. | 424/53 |
| 5,449,403 | 9/1995 | Andrean et al. | 106/498 |
| 5,456,902 | 10/1995 | Williams et al. | 424/49 |
| 5,478,551 | 12/1995 | Busch, Jr. | 424/61 |
| 5,484,586 | 1/1996 | Bedard | 424/61 |
| 5,534,265 | 7/1996 | Fowler et al. | 424/489 |
| 5,554,358 | 9/1996 | Williams et al. | 424/49 |
| 5,567,428 | 10/1996 | Hughes | 424/401 |
| 5,622,691 | 4/1997 | Tricaud et al. | 424/62 |

FOREIGN PATENT DOCUMENTS 8-119836  5/1996  Japan .

OTHER PUBLICATIONS

*Modern Cosmeticology—The Principles and Practice of Modern Cosmetics* by Ralph G. Harry, Chemical Publishing Co., Inc., 1940, pp. 264–266 and title page.

*The Chemical Formulary,* H. Bennett, ed., Chemical Publishing Co., Inc., 1951, pp. 90–91, & title page.

*Cosmetic Safety—A Primer for Cosmetic Scientists,* by James H. Whittam, ed., pp. 272–277, 283, Marcel Dekker, Inc.

*Formulating with Hydrogen Peroxide,* Wetmur et al., Happi, pp. 52, 54, 56, Feb. 1997.

Brochure entitled *Hydrogen Peroxide —Consumer Products,* by Solvay Interox, 12 pps.

Kirk–Othmer Encyclopedia of Chemical Technology, ed. 4, V. 13, *Hydrogen Peroxide,* pp. 964–966; 984–986; 989–900.

*Harry's Cosmeticology,* Pp. 371, 373 and 374.

*Hydrogen Peroxide,* Merck Index, ed. 11, 4725–4727.

*Successful Use of Topical Vitamin E Solution in the Treatment of Nail Changes in Yellow Nail Syndrome,* Williams et al., Arch Dermatol—vol. 127, Jul. 1991, pp. 1023–1028.

*Fingernail Elongators and Accessory Nail Preparations,* p. 575, Belsam & Sagarin: Cosmetics Science Technology, 2d ed.

Ullmann's Ency. of Industrial Chemistry, pp. 384, 392, vol. A8, *Detergents.*

Ullmann's Ency. of Industrial Chemistry, ed. 5, pp. 194, 197, *Peroxo Compounds, Inorganic,* vol. A19.

Kirk–Othmer Encyclopedia of Chemical Technology, ed. 3, V. 13, *Hydrogen Peroxide,* pp. 14–15, 30–31.

Kirk–Othmer Encyclopedia of Chemical Technology, ed. 3, V. 3, *Bleaching Agents,* pp. 944–945, 957.

Zimmerman's Complete Guide to Nonprescription Drugs, pp. 692–693.

*Bleaching* by Hans Ulrich Suss, pp. 191–199, Ullmann's Ency. of Industrial Chemistry.

Excerpt from Solvay Interox brochure entitled "Hydrogen Peroxide in Consumer Products", Page 2, copyright 1996.

Hydrogen Peroxide Technical Data Sheets, Ultra Cosmetic and PeroxClean Hydrogen Peroxide, 3 pages (1996).

Material Safety Data Sheet, Ultra Cosmetic Hydrogen Peroxide, effective Mar. 8, 1996, 14 pages.

*Primary Examiner*—Thurman K. Page
*Assistant Examiner*—Sharon Howard
*Attorney, Agent, or Firm*—Ohlandt, Greeley, Ruggiero & Perle

[57] ABSTRACT

A cosmetic composition for treating nails, including from about 0.01 weight percent to about 10.0 weight percent stabilized hydrogen peroxide; a pH adjusting agent in an amount sufficient to maintain said cosmetic composition at a pH of from about 8.0 to about 8.5; and water.

25 Claims, No Drawings

NAIL BLEACH

The present invention relates generally to a composition for bleaching stained fingernails. More particularly, this invention relates to a cosmetic composition containing a stabilized hydrogen peroxide that can be applied to stained fingernails to remove yellowing and stains.

BACKGROUND OF THE INVENTION

The cosmetic appearance of fingernails has long been a matter of concern to consumers. Nail polishes and artificial fingernails are among the popular cosmetic treatments applied to the nails (fingernails or toenails, hereinafter collectively called "nails"). However, regular or even occasional use of such products can leave the natural nail yellowed and stained. In addition, coffee, cigarettes, certain medications, and the use of harsh chemicals in the home, may also leave the nail undesirably yellow and uneven in color.

Products are available on the market that coat the nail with a slight purple tint, in the manner of a nail polish, to counteract the yellow coloring of the nail. However, just like nail polish, these products have limited durability, require frequent reapplication, and function only to mask the nail problem, not to correct it. Such products also do not improve the condition of the cuticle.

In addition, home bleaching remedies are also known. These remedies use oxidizing agents such as hydrogen peroxide, in one of two types of compositions. The first of these is a stable acidic composition, in which the bleaching effectiveness of the hydrogen peroxide is curtailed. In a lower pH solution, the oxidizing activity of the hydrogen peroxide is reduced, and the composition does not "wet out" or disperse as effectively on the nail, limiting contact between the hydrogen peroxide and the stain. Alternatively, higher pH compositions are known, however these typically require the addition of an activator. This activator must be added immediately prior to use, thus necessitating a two-phase composition.

Accordingly, a need exists for a single phase, shelf-stable nail bleaching product that effectively bleaches and removes nail stains and yellowing.

SUMMARY OF THE INVENTION

Against the foregoing background, it is a primary object of the present invention to provide a shelf-stable nail cosmetic composition for removing nail stains and yellowing.

It is a further object of the present invention to provide a nail bleaching cosmetic that is premixed and does not require additional preparation by the user prior to application.

It is another object of the present invention to provide a cosmetic composition that softens and removes dead cuticle skin.

It is yet another object of the present invention to provide a cosmetic composition having the foregoing attributes that is not harmful to the nail or to healthy cuticle tissue.

To the accomplishment of the foregoing objects and advantages, the present invention, in brief summary, comprises a nail bleach containing stabilized hydrogen peroxide in an acceptable carrier. More preferably, the nail bleach also includes a pH adjusting agent to maintain the composition at a higher pH. A preferred cosmetic composition for treating nails includes from about 0.01 percent by weight or weight percent to about 10 weight percent stabilized hydrogen peroxide, a pH adjusting agent in an amount sufficient to maintain said cosmetic composition at a pH from about 8.0 to about 8.5, and water.

DESCRIPTION OF THE PREFERRED EMBODIMENTS

The present invention provides a nail bleach composition that is premixed, shelf-stable and safe to the nails and healthy cuticle skin. In addition, regular use of the claimed composition softens and removes dead cuticle skin, further improving the appearance of the nails. As discussed herein, shelf-stable cosmetic compositions are those in which the oxidizing agent does not degrade over normal product distribution periods, storage periods and temperature extremes to the point that it is no longer active.

The stable nail bleach compositions of the present invention include stabilized hydrogen peroxide, in a cosmetically acceptable carrier. These compositions are not multi-component systems, but include only a single preformulated component. They require no mixing or activation immediately prior to use. They can be packaged in a standard jar or other dispenser and can be applied directly to the nail and cuticle. Preferably, the composition is used on a regular basis, such as once daily, until results are achieved. If the nails are continually being stained, due to daily smoking, for example, the product can be applied to the nails indefinitely.

The stabilized hydrogen peroxide of the present invention is hydrogen peroxide in a stabilized form such that contact with aqueous carriers and extended storage do not result in any significant deactivation of the hydrogen peroxide. The stabilized hydrogen peroxide functions as the bleaching agent in the nail bleach of the present invention. At very low levels, it will have little effect on nail stains, and at high levels it will be irritating or harmful to the nail and surrounding skin. Accordingly, the stabilized hydrogen peroxide is preferably present at about 0.01 to about 10 weight percent of the composition, and more preferably at about 2 to about 5 weight percent of the composition. Most preferably, the stabilized hydrogen peroxide is present at about 3.0 to about 3.5 weight percent. The process and components of the stabilized hydrogen peroxide solution are proprietary. A preferred stabilized hydrogen peroxide, Ultra Cosmetic Peroxide (35% actives), is available from Solvay Interox. For the purposes of the present invention, such proprietary stabilized hydrogen peroxides are distinguished from hydrogen peroxide-containing compositions that are stabilized only due to their low pH.

The preferred nail bleach of the present invention includes a pH adjusting agent in order to preferably maintain the pH of the composition in the range of about 6 to about 9. More preferable is a basic pH (greater than 7), most preferably about 8.0 to about 8.5. Any cosmetically acceptable pH adjusting agent or agents can be used in the compositions of the present invention, provided they do not contain contaminants at a level sufficient to decompose the hydrogen peroxide. It is believed that the preferred slight alkalinity of the nail bleach is the primary source of its ability to effectively soften cuticles. The pH adjusting agent also acts to accelerate the bleaching process. The pH adjusting component concentration, as well as water level, can be adjusted to achieve this desired pH range. When sodium hydroxide is used as the pH adjusting agent, the most preferred pH in the range of about 8.0 to about 8.5 has been achieved.

To provide a cosmetically pleasing product, and to aid in delivering the stabilized hydrogen peroxide to the nail and cuticle area, a thickener is preferably added to the nail bleach composition of the present invention. Any cosmetic thickener suitable for use with an aqueous peroxide composition may be used in the present composition. The thickener is preferably present at a range of about 0.1 to about 20 weight percent, with a range of about 1 to about 5 weight percent being more preferred. Thickeners such as acrylic acid polymers (e.g. Carbopol) and Salcare SC90, a steareth-10 alkyl ether/acrylate copolymer provided by Allied Colloids Inc., are preferred, with Salcare SC90 being most preferred.

A fragrance may be added to the nail bleach composition, to enhance its appeal and acceptability. The fragrance is preferably present at up to about 2 weight percent, with a range of about 0.0001 to about 1.0 weight percent being most preferred. Any suitable cosmetic fragrance may be used.

When certain thickeners are used, the addition of a viscosity stabilizer to the composition may further improve the aesthetics of the finished product. Viscosity stabilizers are useful in the nail bleach compositions of the present invention, to enhance the stability of the composition over time. The viscosity stabilizers that are preferred for use in the compositions of the present invention are surfactants that can survive in contact with oxidizing agents. The viscosity stabilizers are preferably present at up to about 25 weight percent, with a weight percent of up to about 10 being more preferred. Most preferred viscosity stabilizers include sodium lauryl sulfate (which also acts as a degreaser) and Pluronic F127, a polyoxypropylene/polyoxyethylene block copolymer provided by BASF Corporation (which also acts as an anti-irritant), alone or in combination. Surfactants can also function in compositions of the present invention to reduce the surface tension of the composition, to enhance "wet out" or dispersion of the hydrogen peroxide on the nail. Accordingly, surfactants can be used in compositions of the present invention that do not contain thickeners.

Additional ingredients such as vitamins, glycerin, healing and treatment agents may also be added to the nail bleach composition.

Certain active ingredients such as stabilized hydrogen peroxide and a pH adjusting agent, sodium hydroxide, are provided in solution containing a percentage of active ingredients. For example, the hydrogen peroxide solution of the foregoing preferred embodiment is present at 9.71 weight percent of 35% active solution. Accordingly, stabilized hydrogen peroxide, as the term is used in the appended claims, is present at about 3.4 weight percent (0.35×0.0971= 0.034).

The following is a preferred exemplary nail bleach according to the present invention:

EXAMPLE 1

NAIL BLEACH

|  | Wt. % |
| --- | --- |
| Ultra cosmetic peroxide (35% active) | 9.71 |
| Deionized water | 82.42 |
| Sodium hydroxide (25% active) | 0.77 |
| Steareth-10 alkyl ether/ acrylate copolymer | 2.00 |
| Fragrance | 0.1 |

EXAMPLE 1-continued

NAIL BLEACH

|  | Wt. % |
| --- | --- |
| Polyoxypropylene/polyoxyethylene block copolymer | 5.00 |

Other preferred examples according to the present invention include:

1) the product of Example 1 formulated with the added viscosity stabilizer sodium lauryl sulfate (at 1.9 wt % plus 0.1 wt % sodium chloride—the water level is accordingly decreased by 2.00 wt %); and 2) the product of Example 1 formulated with the added viscosity stabilizer sodium lauryl sulfate (at 1.9 wt % plus 0.1 wt % sodium chloride), but without the viscosity stabilizer polyoxypropylene/polyoxyethylene block copolymer (the water level is accordingly increased by 3.00 weight percent).

While the improved cosmetic appearance of fingernails is a primary object of the present invention, it is evident that stained or yellowed toenails, for example, can also be treated by the claimed compositions and methods. Toenails are also commonly coated with nail polish, and can also be stained by such things as medications or dyes in socks or other footwear.

The invention having been thus described with particular reference to the preferred forms thereof, it will be obvious that various changes and modifications may be made therein without departing from the spirit and scope of the invention as defined in the appended claims.

What we claim is:

1. A shelf-stable nail bleach composition comprising:
   from about 0.01 weight percent to about 10 weight percent alkaline-stable hydrogen peroxide; and a pH adjusting agent in an amount sufficient to bring said composition to an alkaline pH.

2. The nail bleach composition of claim 1, wherein said alkaline-stable hydrogen peroxide is present at about 2 weight percent to about 5 weight percent.

3. The nail bleach composition of claim 1, wherein said pH adjusting agent is sodium hydroxide.

4. The nail bleach composition of claim 3, wherein said sodium hydroxide is present at about 0.8 weight percent.

5. The nail bleach composition of claim 1, wherein said nail bleach composition has a basic pH.

6. The nail bleach composition of claim 5, wherein said pH is from about 8.0 to about 8.5.

7. The nail bleach composition of claim 1, fur her comprising a thickener.

8. The nail bleach composition of claim 7, wherein said thickener is present from about 0.1 to about 20 weight percent.

9. The nail bleach composition of claim 8, wherein said thickener is present from about 1 to about 5 weight percent.

10. The nail bleach of claim 7, wherein said thickener is copolymeric.

11. The nail bleach of claim 10, wherein said thickener is a steareth-10 alkyl ether/acrylate copolymer.

12. The nail bleach of claim 1, further comprising a viscosity stabilizer.

13. The nail bleach of claim 12, wherein said viscosity stabilizer is present at up to about 25 weight percent.

14. The nail bleach of claim 12, wherein said viscosity stabilizer is present at up to about 10 weight percent.

15. The nail bleach of claim 12, wherein said viscosity stabilizer is selected from the group consisting of sodium lauryl sulfate, polyoxypropylene/polyoxyethylene block copolymer and a mixture thereof.

16. A cosmetic composition for treating nails, comprising:
   from about 0.01 weight percent to about 10 weight percent stabilized hydrogen peroxide;
   a pH adjusting agent in an amount sufficient to maintain said cosmetic composition at a pH from about 8.0 to about 8.5; and
   water.

17. The cosmetic composition of claim 16, further comprising a thickener.

18. The cosmetic composition of claim 16, further comprising a viscosity stabilizer.

19. The cosmetic composition of claim 16, wherein said pH adjusting agent is sodium hydroxide.

20. The cosmetic composition of claim 17, wherein said odium hydroxide is present at about 0.8 weight percent.

21. The cosmetic composition of claim 17, wherein said thickener is copolymeric.

22. The cosmetic composition of claim 21, wherein said thickener is a steareth-10 alkyl ether/acrylate copolymer.

23. The cosmetic composition of claim 18, wherein said viscosity stabilizer is selected from the group consisting of sodium lauryl sulfate, polyoxypropylene/polyoxyethylene block copolymer and a mixture thereof.

24. A method of removing stains from nails, comprising:
   applying to the nails a shelf-stable nail bleach composition comprising:
      from about 0.01 weight percent to about 10 weight percent alkaline-stable hydrogen peroxide;
      a pH adjusting agent in an amount sufficient to bring said cosmetic composition to an alkaline pH;
   wherein said composition is substantially free from polysiloxane-grafted adhesive polymer.

25. A method of improving cuticles, comprising:
   applying to the cuticles a composition according to claim 1.

* * * * *